(12) United States Patent
Rajagopalan

(10) Patent No.: US 9,822,117 B2
(45) Date of Patent: Nov. 21, 2017

(54) PYRIDOINDOLOBENZ[B,D]AZEPINE DERIVATIVES AND USES THEREOF

(71) Applicant: Daya Drug Discoveries, Inc., St. Peters, MO (US)

(72) Inventor: Parthasarathi Rajagopalan, St. Peters, MO (US)

(73) Assignee: DAYA DRUG DISCOVERIES, INC., St. Louis, MO (US)

( * ) Notice: Subject to any disclaimer, the term of this patent is extended or adjusted under 35 U.S.C. 154(b) by 26 days.

(21) Appl. No.: 14/770,476

(22) PCT Filed: Mar. 2, 2014

(86) PCT No.: PCT/US2014/019752
§ 371 (c)(1),
(2) Date: Aug. 26, 2015

(87) PCT Pub. No.: WO2014/137848
PCT Pub. Date: Sep. 12, 2014

(65) Prior Publication Data
US 2016/0002237 A1  Jan. 7, 2016

Related U.S. Application Data

(60) Provisional application No. 61/772,046, filed on Mar. 4, 2013.

(51) Int. Cl.
*A61K 31/55* (2006.01)
*C07D 471/16* (2006.01)
*C07D 487/16* (2006.01)

(52) U.S. Cl.
CPC .................. *C07D 471/16* (2013.01)

(58) Field of Classification Search
CPC ..... A61K 31/55; C07D 471/16; C07D 487/16
USPC ...................... 514/214.02; 540/579
See application file for complete search history.

(56) References Cited

U.S. PATENT DOCUMENTS

| 3,983,123 | A | * | 9/1976 | Adams | .......................... 540/579 |
| 4,219,550 | A | * | 8/1980 | Rajagopalan | ........ C07D 498/16 514/211.1 |
| 4,438,120 | A | * | 3/1984 | Rajagopalan | ........ C07D 243/38 514/219 |

* cited by examiner

*Primary Examiner* — Brenda Coleman
(74) *Attorney, Agent, or Firm* — Raghavan Rajagopalan

(57) ABSTRACT

The present invention discloses pyridoindolobenz[b,d] azepines compositions of Formula 1, wherein Y is a single bond or a double bond. A and B are independently —$(CH_2)_n$—; and 'n' varies from 0 to 3. $R^1$ to $R^{10}$ are various electron donating, electron withdrawing, hydrophilic, or lipophilic groups selected to optimize the physicochemical and biological properties of compounds of Formula I.

51 Claims, 6 Drawing Sheets

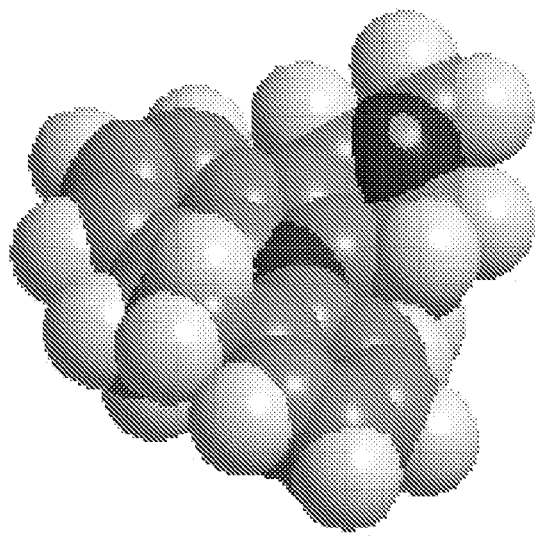
Energy-minimized structure of compound 6a (DDD-025).
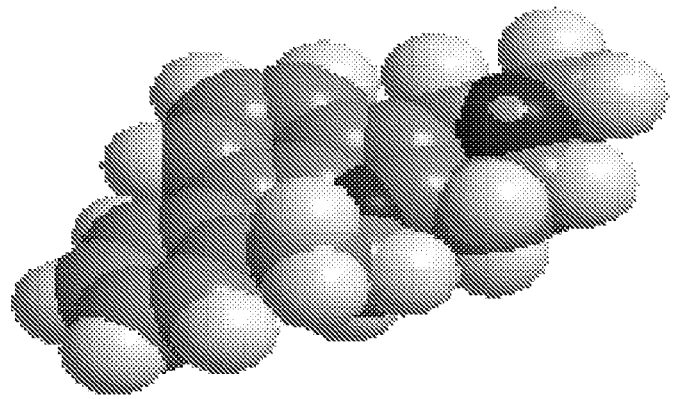
Energy-minimized structure of compound 13 (DDD-028).
Figure 1. Space-filling models of compounds 6a (prior art) and 13 (present invention).

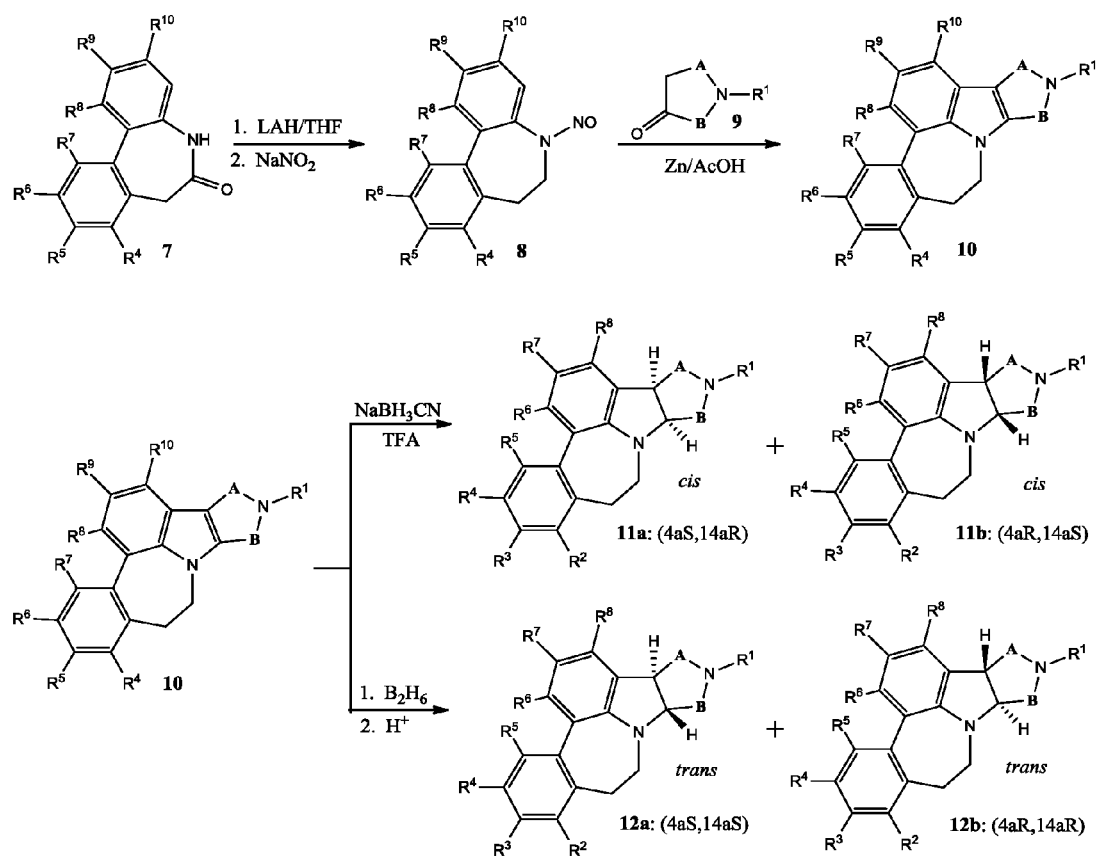
Figure 2. Synthesis of Pyridoindolobenz[*b,d*]azepine derivatives.

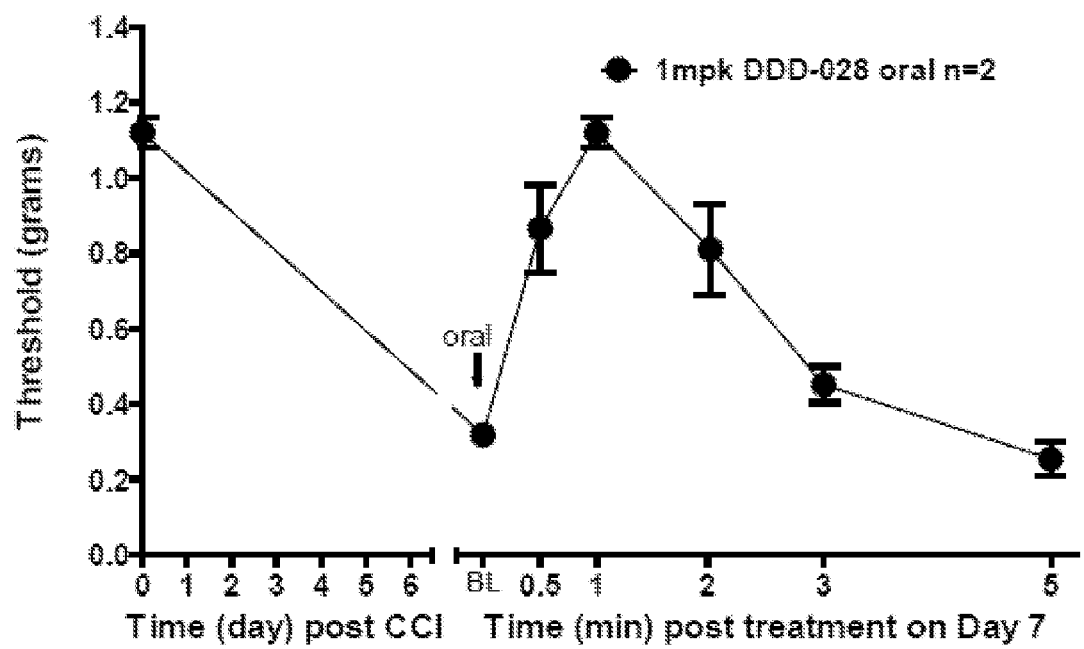
Figure 3. Mice CCI neuropathic pain model results (oral administration).

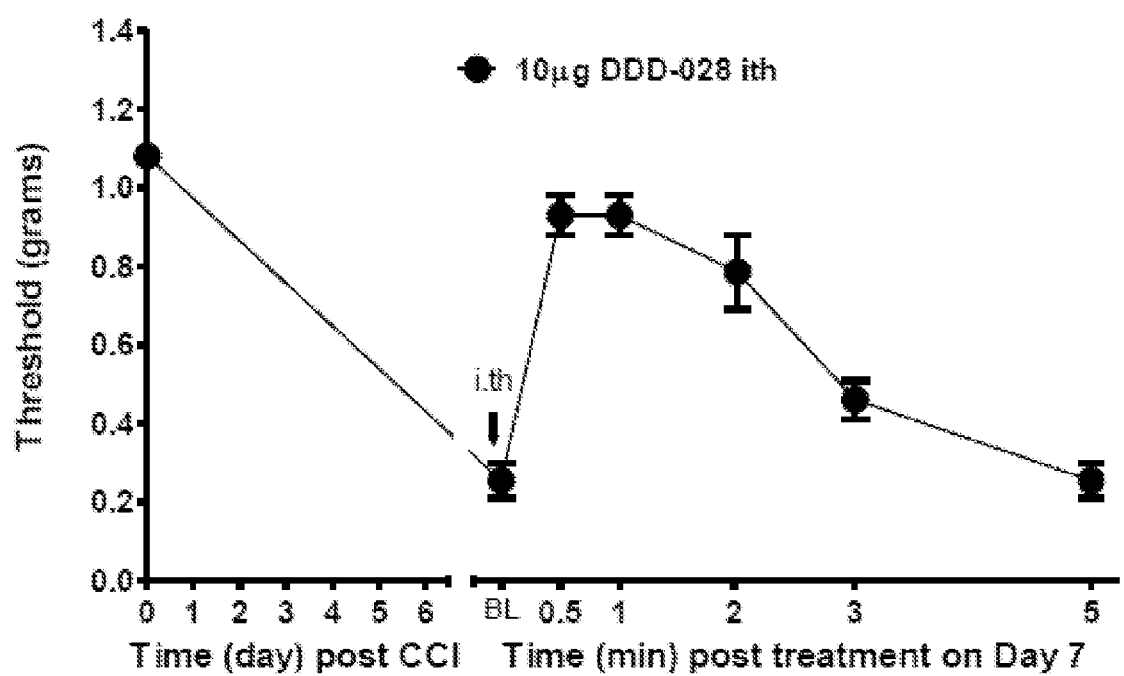
Figure 4. Mice CCI neuropathic pain model results (intathecal administration)

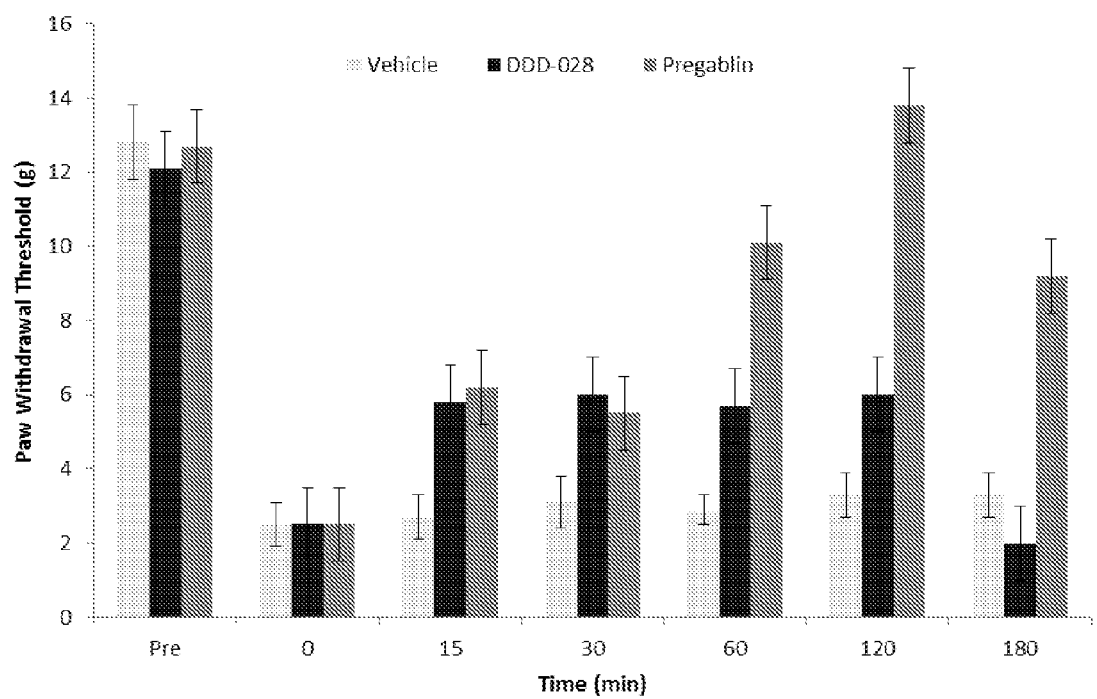
Figure 5. Rat SNL neuropathic pain model results (oral administration).

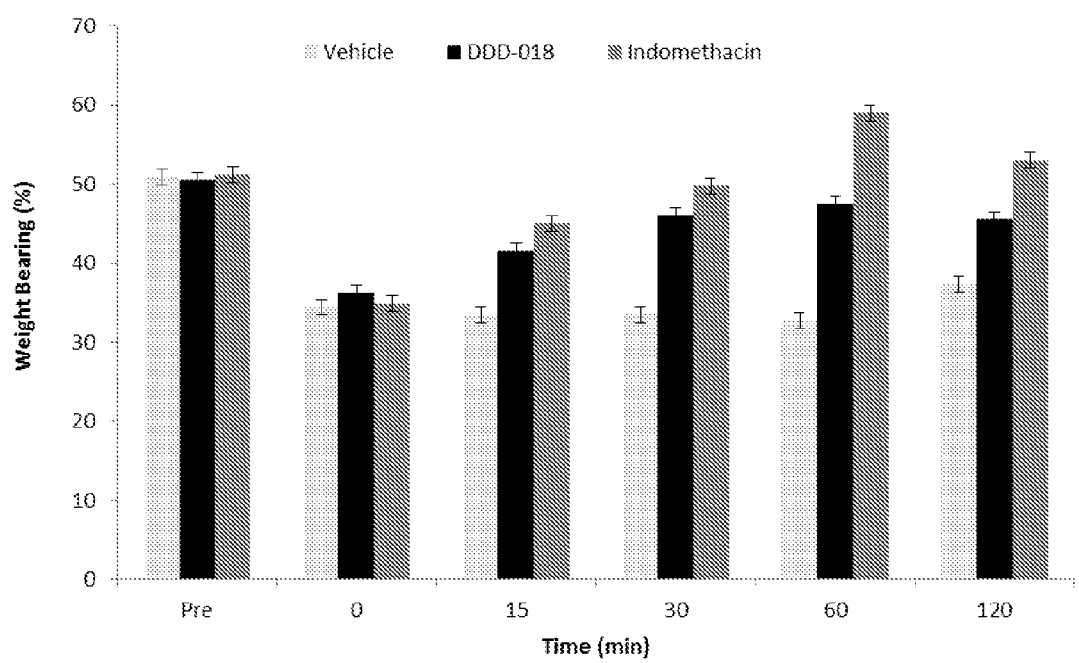
Figure 6. Rat CFA-induced inflammatory pain model results (oral administration).

PYRIDOINDOLOBENZ[B,D]AZEPINE DERIVATIVES AND USES THEREOF

This application claims benefit of priority based on provisional application No. 61/772,046 filed on Mar. 4, 2013.

FIELD OF INVENTION

This invention relates to novel pentacyclic pyridoindolobenz[b,d]azepine derivatives for the treatment of neurological disorders and cancer.

PRELIMINARY NOTE

Various prior art references in the specification are indicated by italicized Arabic numerals in brackets. Full citation corresponding to each reference number is listed at the end of the specification, and is herein incorporated by reference in its entirety in order to describe fully and clearly the state of the art to which this invention pertains.

Unless otherwise specified, all technical terms and phrases used herein conform to standard organic and medicinal chemistry nomenclature established by International Union of Pure and Applied Chemistry (IUPAC), the American Chemical Society (ACS), and other international professional societies. The rules of nomenclature are described in various publications, including, "Nomenclature of Organic Compounds," [1], and "Systematic Nomenclature of Organic Chemistry" [2], which are herein incorporated by reference in their entireties.

BACKGROUND

Neurological disorders comprise several major diseases as described in the Diagnostic and Statistical Manual of Mental Disorders (DSM IV-R) [3]. It is well-established that a particular neurological disorder may involve complex interactions of multiple neuroreceptors and neurotransmitters, and, conversely, a single neuroreceptor may be implicated in several disorders, both neurological and non-neurological. For example, the serotonin receptor is implicated in numerous disorders such as depression, anxiety, pain (both acute and chronic), etc.; the dopamine receptor is implicated in movement disorder, addiction, autism, etc; and the sigma receptors are involved in pain (both acute and chronic), and cancer. Many of the receptors that are found in the brain are also found in other areas of the body, including gastrointestinal (GI) tract, blood vessels, and muscles, and elicit physiological response upon activation by the ligands.

The rational drug design process is based on the well-established fundamental principle that receptors, antibodies, and enzymes are multispecific, i.e., topologically similar molecules will have similar binding affinity to these biomolecules, and, therefore, are expected to elicit similar physiological response as those of native ligands, antigens, or substrates respectively. Although this principle, as well as molecular modeling and quantitative structure activity relationship studies (QSAR), is quite useful for designing molecular scaffolds that target receptors in a "broad sense," they do not provide sufficient guidance for targeting specific receptor subtypes, wherein subtle changes in molecular topology could have substantial impact on receptor binding profile. Moreover, this principle is inadequate for predicting in vivo properties of any compound; hence, each class of compound needs to be evaluated in its own right for receptor subtype affinity and selectivity, and in in vivo animal models to establish efficacy and toxicity profiles. Thus, there is a sustained need for the discovery and development of new drugs that target neuroreceptor subtypes with high affinity and selectivity in order to improve efficacy and/or minimize undesirable side effects.

Serotonin and sigma receptors are widely distributed throughout the body. To date, fourteen serotonin and two sigma receptor subtypes have been isolated, cloned, and expressed. Serotonin receptors mediate both excitatory and inhibitory neurotransmission, and also modulate the release of many neurotransmitters including dopamine, epinephrine, nor-epinephrine, GABA, glutamate and acetylcholine as well as many hormones such as oxytocin, vasopressin, corticotrophin, and substance P [4, 5]. During the past two decades, serotonin receptor subtype selective compounds have been a rich source of several FDA-approved CNS drugs. Most of these serotonin receptor subtypes have been focus of research in the past couple of decades and this effort has led to the discovery of important therapeutics like Sumatriptan (5-HT$_{1B/1D}$ agonist) for the treatment of migraine, Ondansetron (5-HT$_3$ agonist) for the treatment of radiation or chemotherapy-induced nausea and vomiting, and Zyprexa (5-HT$_{2A}$/D$_2$ antagonist) for the treatment of schizophrenia. Therapeutic targets have been identified for 5-HT$_4$ (learning and memory) [6], 5-HT$_{5A}$ (cognition, sleep) [7], 5-HT$_6$ (learning, memory) [8] and 5-HT$_7$ (pain and depression) [9, 10], and some selective ligands have been prepared for all of these receptors with the exception of 5-HT$_{5A}$. In contrast, the sigma receptors have not received as much attention as the serotonin subtypes. Only recently has there been a substantial interest in sigma receptors, particularly due to its importance in pain and cancer. In particular, $\sigma_1$ receptor is implicated in pain, and $\sigma_1$ antagonists have been shown to have antinociceptive properties [11]. On the other hand, $\sigma_2$ receptor is overexpressed in highly proliferating cells such as cancer cells, and activation of this receptor induces apoptosis. Hence, $\sigma_2$ agonists may have potential use as anticancer agents [12].

Numerous receptors are involved in the pain process, and currently, there is clear evidence that both 5-HT$_7$ and $\sigma_1$ receptors directly involved in pain pathway, and selective ligand that target these receptor subtypes have been prepared and tested. For example, AS-19 (1), a selective 5-HT$_7$ agonist and BD-1063 (2), a $\sigma_1$ antagonist, have been shown to be

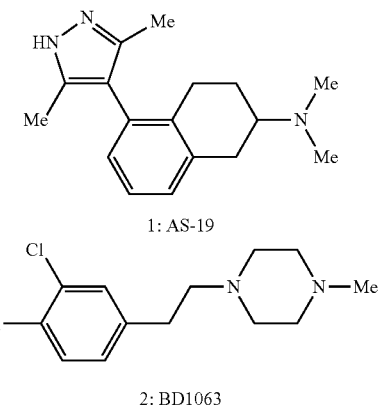

1: AS-19

2: BD1063 effective in inhibiting pain [9, 11]. However, there is no FDA approved medication based on 5-HT$_7$ or sigma receptors, albeit many agents are in preclinical and clinical development stages. Thus, new medication for the treatment of chronic pain is in great need, particularly due to increasing aging and diabetic populations.

Rajagopalan[13, 14] and Adams et al. [15] disclosed the pentacyclic scaffolds incorporating the γ-carboline pharmacophore 3-6, where the two phenyl rings are fused at the 'b' and 'f' positions in the 7-membered D-ring. In particular, the sulfur analog 6b has been shown recently to have atypical antipsychotic properties [16]. However, other pentacyclic analogs, where the E-phenyl ring being fused at other positions in the 7-memebered D-ring, have not been disclosed.

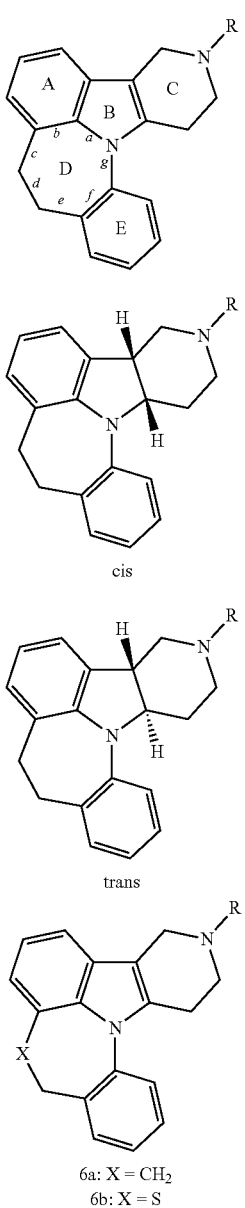

positions in the 7-membered D-ring. A and B are independently —$(CH_2)_n$—; and 'n' varies from 0 to 3. $R^1$ to $R^{10}$ are various electron donating, electron withdrawing, hydrophilic, or lipophilic groups selected to optimize the physicochemical and biological properties of compounds of Formula I. These properties include receptor binding, receptor selectivity,

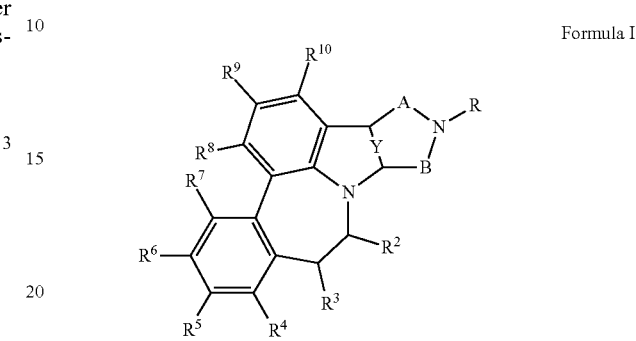

Formula I tissue penetration, lipophilicity, toxicity, bioavailability, and pharmacokinetics. As will be demonstrated later, some of the compounds of the present invention exhibit favorable in vivo biological properties that could not be ascertained from the prior art literature. Compounds of the present invention are useful for the treatment of pain and other neurological disorders. Moreover, as mentioned before, the receptor binding and pharmacological properties are very sensitive to the overall molecular topology, and these properties cannot be predicted just from the inspection of molecular structure. The pentacyclic structure 6a is triangular, whereas the pentacyclic structure 13 of the present invention derived from Formula I is elliptical (FIG. 1) in overall shape; hence, the biological activities of the compounds derived from these two scaffolds are expected to be different.

BRIEF DESCRIPTION OF FIGURES

FIG. 1. Space-filling models of compound 6a and compound 13.

FIG. 2. General synthetic scheme for pyridoindolobenz [b,d]azepines.

FIG. 3. Evaluation of DDD-028 in mouse sciatic nerve chronic constriction injury (CCI) model of neuropathic pain (oral administration).

FIG. 4. Evaluation of DDD-028 in mouse sciatic nerve chronic constriction injury (CCI) model of neuropathic pain (intrathecal administration).

FIG. 5. Evaluation of DDD-028 in rat spinal nerve ligation (SNL) model of neuropathic pain (oral administration).

FIG. 6. Evaluation of DDD-028 in rat Complete Freund's adjuvant (CFA)-induced inflammation pain model (oral administration)

SUMMARY

Accordingly, the present invention relates to novel pentacyclic γ-carboline scaffold represented by Formula I, wherein the two phenyl groups are fused at the 'b' and 'd'

DETAILED DESCRIPTION

The present invention relates to pentacyclic compounds of Formula I, wherein

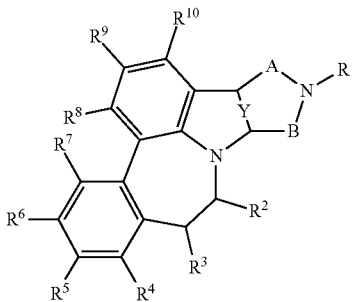

Formula I

Y is a single bond or a double bond;

A and B are independently —($CH_2$)$_n$—, and subscript 'n' varies from 0 to 3;

$R^1$ is selected from the group consisting of hydrogen, $C_1$-$C_{10}$ alkyl, $C_1$-$C_{10}$ hydroxyalkyl, $C_5$-$C_{10}$ aryl unsubstituted or substituted with electron donating groups (EDG) or electron withdrawing groups (EWG), $C_1$-$C_{15}$ aroylalkyl, $C_1$-$C_{10}$ alkoxycarbonylalkyl, $C_1$-$C_{10}$ carbamoylalkyl, and $C_5$-$C_{10}$ arylalkyl unsubstituted or substituted with EDG or EWG;

$R^2$ is selected from the group consisting of hydrogen, $C_1$-$C_{10}$ alkyl, $C_5$-$C_{10}$ aryl unsubstituted or substituted with EDG or EWG, and $C_5$-$C_{10}$ arylalkyl unsubstituted or substituted with EDG or EWG;

$R^3$ to $R^{10}$ are independently selected from the group consisting of hydrogen, $C_1$-$C_{10}$ alkyl, hydroxyl, $C_1$-$C_{10}$ alkoxyl, —$NR^{11}R^{12}$, $C_1$-$C_{10}$ hydroxyalkyl, halogen, trihaloalkyl, cyano, carboxyl, $C_1$-$C_{10}$ acyl, $C_1$-$C_{10}$ alkoxyalkyl; $C_1$-$C_{10}$ alkoxycarbonyl; $C_5$-$C_{10}$ aryl unsubstituted or substituted with EDG or EWG, and $C_5$-$C_{10}$ arylalkyl unsubstituted or substituted with EDG or EWG;

$R^{11}$ and $R^{12}$ are independently hydrogen or $C_1$-$C_{10}$ alkyl, and may optionally be tethered together from a heterocylic ring.

The phrase, 'electron donating group (EDG)' and 'electron withdrawing group (EWG)' are well understood in the art. EDG comprises alkyl, hydroxyl, alkoxyl, amino, acyloxy, acylamino, mercapto, alkylthio, and the like. EWG comprises halogen, acyl, nitro, cyano, carboxyl, alkoxycarbonyl, and the like.

The first embodiment of the present invention is represented by Formula I, wherein, Y is a double bond;

A and B are —($CH_2$)$_n$—, and 'n' varies from 0 to 3;

$R^1$ is selected from the group consisting of hydrogen, $C_1$-$C_{10}$ alkyl, $C_1$-$C_{10}$ hydroxyalkyl, $C_5$-$C_{10}$ aryl unsubstituted or substituted with electron donating or electron withdrawing groups, $C_1$-$C_{15}$ aroylalkyl, $C_1$-$C_{10}$ alkoxycarbonylalkyl, $C_1$-$C_{10}$ carbamoylalkyl, and $C_5$-$C_{10}$ arylalkyl unsubstituted or substituted with EDG or EWG;

$R^2$ to $R^{10}$ are independently selected from the group consisting of hydrogen, $C_1$-$C_{10}$ alkyl, hydroxyl, $C_1$-$C_{10}$ alkoxyl, —$NR^{11}R^{12}$, $C_1$-$C_{10}$ hydroxyalkyl, halogen, trihaloalkyl, cyano, carboxyl, $C_1$-$C_{10}$ acyl, $C_1$-$C_{10}$ alkoxyalkyl; $C_1$-$C_{10}$ alkoxycarbonyl; $C_5$-$C_{10}$ aryl unsubstituted or substituted with EDG or EWG, and $C_5$-$C_{10}$ arylalkyl unsubstituted or substituted with EDG or EWG; and $R^{11}$ and $R^{12}$ are independently hydrogen or $C_1$-$C_{10}$ alkyl.

The second embodiment is represented by Formula I, wherein

Y is a double bond;

A is —$CH_2$—;

B is —$CH_2CH_2$—;

$R^1$ is hydrogen, $C_1$-$C_{10}$ alkyl, $C_5$-$C_{10}$ arylalkyl; $C_1$-$C_{15}$ aroylalkyl, $C_1$-$C_{10}$ carbamoylalkyl; and each of $R^2$, $R^3$, $R^4$, $R^5$, $R^6$, $R^7$, $R^8$, $R^9$, and $R^{10}$ is hydrogen.

The third embodiment of the present invention is represented by Formula I, wherein, Y is a single bond;

A and B are ($CH_2$), and 'n' varies from 0 to 3;

$R^1$ is selected from the group consisting of hydrogen, $C_1$-$C_{10}$ alkyl, $C_1$-$C_{10}$ hydroxyalkyl, $C_5$-$C_{10}$ aryl unsubstituted or substituted with electron donating or electron withdrawing groups, $C_1$-$C_{15}$ aroylalkyl, $C_1$-$C_{10}$ alkoxycarbonylalkyl, $C_1$-$C_{10}$ carbamoylalkyl, and $C_5$-$C_{10}$ arylalkyl unsubstituted or substituted with EDG or EWG;

$R^2$ to $R^{10}$ are independently selected from the group consisting of hydrogen, $C_1$-$C_{10}$ alkyl, hydroxyl, $C_1$-$C_{10}$ alkoxyl, —$NR^{11}R^{12}$, $C_1$-$C_{10}$ hydroxyalkyl, halogen, trihaloalkyl, cyano, carboxyl, $C_1$-$C_{10}$ acyl, $C_1$-$C_{10}$ alkoxyalkyl; $C_1$-$C_{10}$ alkoxycarbonyl; $C_5$-$C_{10}$ aryl unsubstituted or substituted with EDG or EWG, and $C_5$-$C_{10}$ arylalkyl unsubstituted or substituted with EDG or EWG; and $R^{11}$ and $R^{12}$ are independently hydrogen or $C_1$-$C_{10}$ alkyl.

The fourth embodiment is represented by Formula I, wherein

Y is a single bond;

A is —$CH_2$—;

B is —$CH_2CH_2$—;

$R^1$ is hydrogen, $C_1$-$C_{10}$ alkyl, $C_5$-$C_{10}$ arylalkyl; or $C_1$-$C_{15}$ aroylalkyl; and each of $R^2$, $R^3$, $R^4$, $R^5$, $R^6$, $R^7$, $R^8$, $R^9$, and $R^{10}$ is hydrogen.

The compounds belonging to Formula I can be synthesized by the well-known Fisher indole synthesis starting from the tricyclic dibenzazepinones (7) [17] as outlined in FIG. 2. Stereospecific reduction of the double bond in B|C ring junction such as in 10 can be accomplished by $NaBH_3CN$/TFA or with $BH_3$ to give the cis- and trans-reduced compounds 11a,b and 12a,b respectively. Compounds of the present invention may exist as a single stereoisomer or as mixture of enantiomers and diastereomers whenever chiral centers are present. Individual enantiomers can be isolated by resolution methods or by chromatography using chiral columns, and the diastereomers can be separated by standard purification methods such as fractional crystallization or chromatography.

As is well known in the pharmaceutical industry, the compounds of the present invention represented by Formula I, commonly referred to as 'active pharmaceutical ingredient (API)' or 'drug substance', can be prepared as a pharmaceutically acceptable formulation. In particular, the drug substance can be formulated as a salt, ester, or other derivative, and can be formulated with pharmaceutically acceptable buffers, diluents, carriers, adjuvants, preservatives, and excipients. The phrase "pharmaceutically acceptable" means those formulations which are, within the scope of sound medical judgment, suitable for use in contact with the tissues of humans and animals without undue toxicity, irritation, allergic response and the like, and are commensurate with a reasonable benefit/risk ratio. Pharmaceutically acceptable salts include, but are not limited to acetate, adipate, citrate, tartarate, benzoate, phosphate, glutamate, gluconate, fumarate, maleate, succinate, oxalate, chloride, bromide, hydrochloride, sodium, potassium, calcium, magnesium, ammonium, and the like. The formulation technology for manufacture of the drug product is well-known in the art, and are described in "Remington, The Science and Practice of Pharmacy" [18], incorporated herein by reference in its entirety.

The final formulated product, commonly referred to as 'drug product,' may be administered enterally, parenterally, or topically. Enteral route includes oral, rectal, topical, buccal, ophthalmic, and vaginal administration. Parenteral route includes intravenous, intramuscular, intraperitoneal, intrasternal, and subcutaneous injection or infusion. The drug product may be delivered in solid, liquid, or vapor forms, or can be delivered through a catheter for local delivery at a target. Also, it may be administered alone or in combination with other drugs if medically necessary.

Formulations for oral administration include capsules (soft or hard), tablets, pills, powders, and granules. Such formulations may comprise the API along with at least one inert, pharmaceutically acceptable ingredients selected from the following: (a) buffering agents such as sodium citrate or dicalcium phosphate; (b) fillers or extenders such as starches, lactose, sucrose, glucose, mannitol, and silicic acid; (c) binders such as carboxymethylcellulose, alginates, gelatin, polyvinylpyrrolidone, sucrose and acacia; (d) humectants such as glycerol; (e) disintegrating agents such as agar-agar, calcium carbonate, potato or tapioca starch, alginic acid, certain silicates and sodium carbonate; (f) solution retarding agents such as paraffin; (g) absorption accelerators such as quaternary ammonium compounds; (h) wetting agents such as cetyl alcohol and glycerol monostearate; (i) absorbents such as kaolin and bentonite clay and (j) lubricants such as talc, calcium stearate, magnesium stearate, solid polyethylene glycols, sodium lauryl sulfate. and mixtures thereof; (k) coatings and shells such as enteric coatings, flavoring agents, and the like.

Liquid dosage forms for oral administration include pharmaceutically acceptable emulsions, solutions, suspensions, syrups and elixirs. In addition to the API, the liquid dosage forms may contain inert diluents, solubilizing agents, wetting agents, emulsifying and suspending agents, sweetening, flavoring, and perfuming agents used in the art.

Compositions suitable for parenteral injection may comprise physiologically acceptable, sterile aqueous or non-aqueous isotonic solutions, dispersions, suspensions or emulsions, and sterile powders for reconstitution into sterile injectable solutions or dispersions. The compositions may also optionally contain adjuvants such as preserving; wetting; emulsifying; dispensing, and antimicrobial agents. Examples of suitable carriers, diluents, solvents, vehicles, or adjuvants include, but are not limited to water; ethanol; polyols such as propyleneglycol, polyethyleneglycol, glycerol, and the like; vegetable oils such as cottonseed, groundnut, corn, germ, olive, castor and sesame oils, and the like; organic esters such as ethyl oleate and the like; phenol, parabens, sorbic acid, and the like.

Injectable formulations may also be suspensions that contain suspending agents such as ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like. Prolonged absorption of the injectable pharmaceutical form can be brought about by the use of agents delaying absorption, for example, aluminum monostearate and gelatin. Proper fluidity can be maintained, for example, by the use of coating materials such as lecithin, by the maintenance of the required particle size in the case of dispersions, and by the use of surfactants. In some cases, in order to prolong the effect of the drug, it is desirable to slow the absorption of the drug from subcutaneous or intramuscular injection. This can be accomplished by the use of a liquid suspension. Alternatively, delayed absorption of a parenterally administered drug form is accomplished by dissolving or suspending the drug in an oil vehicle.

Injectable depot forms are made by forming microencapsulated matrices of the drug in biodegradable polymers. Depending upon the ratio of drug to polymer and the nature of the particular polymer employed, these compositions release the active ingredient(s) only, or preferentially, in a certain part of the intestinal tract, optionally, in a delayed manner. Thus, the rate of drug release and the site of delivery can be controlled. Examples of embedding compositions include, but are not limited to polylactide-polyglycolide poly(orthoesters), and poly(anhydrides), and waxes. The technology pertaining to controlled release formulations are described in "Design of Controlled Release Drug Delivery Systems," [19] incorporated herein by reference in its entirety.

Formulations for topical administration include powders, sprays, ointments and inhalants. These formulations include the API along with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together. Methods to form liposomes are known in the art and are described in "Liposomes," [20], which is incorporated herein by reference in its entirety.

The compounds of the present invention can also be administered to a patient in the form of pharmaceutically acceptable 'prodrugs.' Prodrugs are generally used to enhance the bioavailability, solubility, in vivo stability, or any combination thereof of the API. They are typically prepared by linking the API covalently to a biodegradable functional group such as a phosphate that will be cleaved enzymatically or hydrolytically in blood, stomach, or GI tract to release the API. A detailed discussion of the prodrug technology is described in "Prodrugs: Design and Clinical Applications," [21] incorporated herein by reference.

The dosage levels of API in the drug product can be varied so as to achieve the desired therapeutic response for a particular patient. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated, the severity of the disorder; activity of the specific compound employed; the specific composition employed, age, body weight, general health, sex, diet of the patient; the time of administration, route of administration, and rate of excretion of the specific compound employed, and the duration of the treatment. The total daily dose of the compounds of this invention administered may range from about 0.0001 to about 1000 mg/kg/day. For purposes of oral administration, more preferable doses can be in the range from about 0.001 to about 5 mg/kg/day. If desired, the effective daily dose can be divided into multiple doses for optimal therapeutic effect.

The following examples illustrate specific embodiments and utilities of the invention, and are not meant to limit the invention. As would be apparent to skilled artisans, various modifications in the composition, operation, and method are possible, and are contemplated herein without departing from the concept and scope of the invention as defined in the claims.

EXAMPLE 1

Preparation of a Compound 13 (DDD-028)

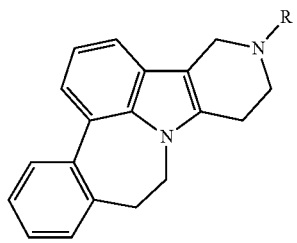

7: DDD-028

Step 1. Dibenzo[b,d]azepine (2.34 g, 12 mmol) in methanol (25 mL), and acetic acid (10 mL) was gently stirred and heated to dissolved all the solids. Thereafter, the solution was cooled to ambient temperature and treated with a concentrated, aqueous solution of $NaNO_2$ (1.38 g, 20 mmol) in water (5 mL) added dropwise over a period of 5 minutes. The reaction was stirred at ambient temperature for 2 hours and treated with water (20 mL). The solid was collected by filtration, washed with water, and dried to give 2.4 g (89%) of the N-nitroso compound. The material was used as such for the next step.

Step 2. A mixture of nitroso compound from Step 1 (448 mg, 2.0 mmol) and N-methyl-4-piperidone hydrochloride (369 mg, 2.4 mmol) in ethanol (4.5 mL) and acetic acid (1.5 mL) at ambient temperature was heated to about 60° C. Thereafter, zinc dust (520 mg, 8.0 mmol) was added in three equal portions allowing 5-10 minutes between the additions. The reaction was then stirred at 55-60° C. for 3 hours. The reaction mixture was cooled to about 0-5° C., diluted and carefully treated with 10% NaOH (4 mL). The reaction mixture was extracted with dichloromethane (3×30 mL). The combined organic layers were washed with brine, dried over anhydrous sodium sulfate, filtered, and the filtrate evaporated in vacuo. The crude material was purified by flash chromatography (silica gel, gradient elution, 0-10% methanol/chloroform over 90 minutes) to furnish 130 mg (36%) of the hydrazone.

Step 3. A mixture of the hydrazone from Step 2 (200 mg, 0.66 mmol) in toluene (2 mL), was treated with 1 M HCl in diethyl ether (1.0 mL, 1.0 mmol), glacial acetic acid (0.5 mL), and p-toluenesulfonic acid (150 mg, 1.6 mmol). The mixture was heated under reflux for 1.5 hours. The reaction mixture was cooled to ambient temperature, treated with 10% NaOH (5 mL), and extracted with ethyl acetate (3×30 mL). The combined organic layers were washed with brine, dried over anhydrous sodium sulfate, filtered, and the filtrate evaporated in vacuo. The crude material was purified by column chromatography using basic alumina (20 g). Elution with ethyl acetate/hexanes gave 164 mg (86%) of the desired product 13. HRMS (ESI): m/z calcd. for $C_{20}H_{21}N_2$ $(M+H)^+$ 289.1699. found, 289.1697.

EXAMPLE 2

(Prophetic): Preparation of Compound 14a,b with Cis-Fused B|C Rings

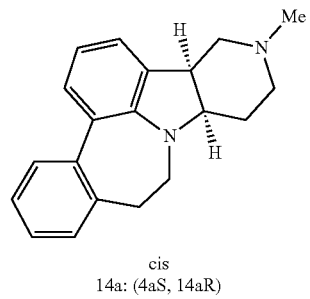

cis
14a: (4aS, 14aR)

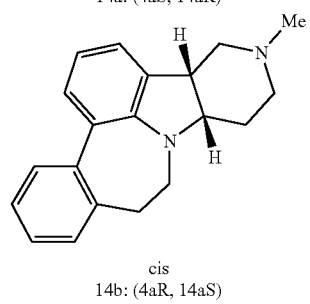

cis
14b: (4aR, 14aS)

A stirred cold solution of compound 13 from Example 1 (2 mmol) in trifluoroacetic acid (6.5 mL) at −5° C., is carefully treated with solid sodium cyanoborohydride (0.125 g, 2.4 mmol). The reaction mixture is then stirred at ambient temperature for 3 h, treated with 6N HCl solution, and heated under reflux for 30 minutes. The solution is cooled to ambient temperature, and excess trifluoroacetic acid is removed in vacuo. The residue is rendered alkaline with 25% NaOH solution (12 mL), and the product extracted with chloroform. The combined organic layers are washed with water and brine, and dried over anhydrous sodium sulfate, filtered, and the filtrate evaporated in vacuo. The crude compound is purified by flash column chromatography or by recrystallization. If necessary, the enantiomers, 14a and 14b, can be separated by methods well-known the art (e.g. chiral column chromatography).

EXAMPLE 3

(Prophetic):Preparation of Compound 15a,b, Trans-Fused B|C Rings

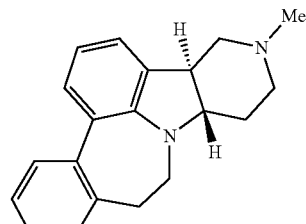

trans
15a: (4aS, 14aS)

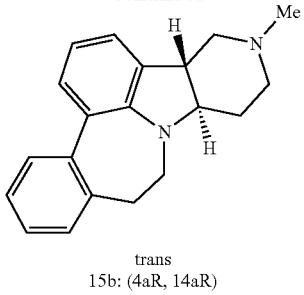

trans
15b: (4aR, 14aR)

The compound 13 from Example 1 (1 mmol) is treated with borane-THF (10 mL, 1.0 M) at ambient temperature, and the mixture is heated under reflux for 1 hour by which time the reaction mixture becomes clear. After cooling to ambient temperature, the solution is treated with water to quench excess reagent borane reagent. The solvents are removed under reduced pressure, and the residue is treated with conc. HCl (7 mL). The mixture is heated at reflux for 3 hours and evaporated to dryness in vacuo, and treated with 10% NaOH solution (10 mL). The product is then extracted with EtOAc, washed with water and brine, dried over anhydrous sodium sulfate, filtered, and the filtrate evaporated to dryness under reduced pressure. The crude product is purified by flash chromatography or recrystallization. If necessary, the enantiomers, 15a and 15b, can be separated by methods well-known the art (e.g. chiral column chromatography).

EXAMPLE 4

In Vitro Receptor Binding Studies of Compounds 6a and 13

The receptor binding data of the prior art compound 6a and the compound of the present invention 13 are given in Table 1. As can be clearly noted, the receptor binding profiles are quite different. Substantial differences in binding to serotonin, α-adrenergic, histamine, and sigma receptors were observed upon changes in the position of the E-ring phenyl group. Most noteworthy is the fact that compound 13 does not bind to any of the dopamine or opioid receptors. Compound 6a displays strong binding to 5-$HT_1$, 5-$HT_{2A}$, 5-$HT_{2B}$, 5-$HT_2$c, $H_1$, and $H_2$, and moderate binding to 5-$HT_6$, $HT_7$, $α_{2A}$, $α_{2B}$, and $α_{2c}$; and 13 displays moderate binding to 5-$HT_{2A}$, 5-$HT_{2B}$, $HT_7$, $α_{1A}$, $α_{1D}$, $α_{2A}$, $α_{2C}$, $σ_1$, and $σ_2$. Compound 6a does not bind to sigma receptors, whereas 13 binds moderately to these receptors.

TABLE 1

| Receptor Binding Data, $K_i$ (nM). | | |
| --- | --- | --- |
| Receptor | 6a | 13 |
| Serotonin | | |
| 5-$HT_{1A}$ | 596 | >10,000 |
| 5-$HT_{1B}$ | 1363 | 1218 |
| 5-$HT_{1D}$ | 85 | 625 |
| 5-$HT_{1E}$ | 4045 | >10,000 |
| 5-$HT_{2A}$ | 24 | 257 |
| 5-$HT_{2B}$ | 87 | 104 |
| 5-$HT_{2c}$ | 10 | >10,000 |
| 5-$HT_3$ | >10,000 | 529 |
| 5-$HT_{5A}$ | 750 | >10,000 |
| 5-$HT_6$ | 155 | >10,000 |
| 5-$HT_7$ | 100 | 195 |
| Dopamine | | |
| $D_1$ | >10,000 | >10,000 |
| $D_2$ | 835 | >10,000 |
| $D_3$ | >10,000 | >10,000 |
| $D_4$ | >10,000 | 1379 |
| $D_5$ | 581 | >10,000 |
| α-Adrenergic | | |
| $α_{1A}$ | 2371 | 286 |
| $α_{1B}$ | 3310 | 2240 |
| $α_{1D}$ | 595 | 293 |
| $α_{2A}$ | 228 | 407 |
| $α_{2B}$ | 413 | 4354 |
| $α_{2C}$ | 173 | 446 |
| β-Adrenergic | | |
| $β_1$ | >10,000 | >10,000 |
| $β_2$ | >10,000 | >10,000 |
| $β_3$ | >10,000 | >10,000 |
| Histamine | | |
| $H_1$ | 50 | >10,000 |
| $H_2$ | 81 | 943 |
| $H_3$ | >10,000 | >10,000 |
| Sigma | | |
| $σ_1$ | 6143 | 220 |
| $σ_2$ | 2234 | 312 |
| Opioid | | |
| δ | >10,000 | >10,000 |
| κ | 2179 | >10,000 |
| μ | >10,000 | >10,000 |
| Muscarinic | | |
| $M_1$ | 4465 | >10,000 |
| $M_2$ | Inactive | >10,000 |
| $M_3$ | 3761 | >10,000 |
| $M_4$ | Inactive | >10,000 |
| $M_5$ | 5167 | >10,000 |
| Transporters | | |
| Dopamine | >10,000 | >10,000 |
| Norepinephrine | >10,000 | 1955 |
| Serotonin | 2190 | 413 |

EXAMPLE 5

In Vivo Evaluation of Compound 13 (DDD-028) in CCI Neuropathic Pain Model in Mice Via Oral and Intrathecal Administration of the Drug DDD-028 was evaluated in chronic constriction injury (CCI) model of neuropathic pain in mice as described by Bennett et al. [22], which is incorporated herein in its entirety. Two male CDI mice (weighing 25-30 g at the time of surgery) were used in this study. The hydrochloride salt of DDD-028 was dissolved in distilled water at 0.15 mg/mL and was administered to the mice to the final dose of 1.0 mg/kg (3.5 gmol/kg) for oral administration (via gavage) or 0.3 mg/kg (1.2 gmol/kg) for intrathecal administration (injection) at peak mechano-allodynia. Baseline PWT measurements (pre-surgery) of the left-hind paw of each animal were taken prior to sciatic nerve ligation. The mice were then anesthetized with 3% isoflurane/100% $O_2$ inhalation, and maintained on 2% isoflurane/100% $O_2$ for the duration of surgery. The left thigh was shaved, scrubbed with Nolvasan, and a small incision (1-1.5 cm in length) was made in the middle of the lateral aspect of the left thigh to expose the sciatic nerve. The nerve was loosely ligated around the entire circumference of the nerve at three distinct sites (spaced 1 mm apart) using silk sutures. The surgical site was closed with a single muscle suture and a skin clip. Peak mechano-allodynia generally develops 7 following surgery. After 7 days post-surgery, Paw Withdrawal Threshold (PWT, g) measurements were taken for each animal to determine the extent of mechanical allodynia. PWT's were measured at 15 min, 30 min, 60 min, 120 min, and 180 min following administration of the drugs or vehicle. No adverse effects were evident in the animals treated with the vehicle or DDD-028. Animals treated with pregabalin exhibited mild sedation 1-3 hours post-administration. Results: DDD-028 completely and rapidly reversed mechano-allodynia, with maximal effect within 30 minutes (FIGS. 3 and 4). DDD-028 had no effect on PWT in contralateral paws. No observable side effects (i.e. lethargy) were noted with DDD-028.

EXAMPLE 6

In Vivo Evaluation of Compound 13 (DDD-028) in SNL Neuropathic Pain Model in Rats Via Oral Administration of the Drug DDD-028 was evaluated in spinal nerve ligation (SNL) model of neuropathic pain in rats as described by Kim et al. [23], which is incorporated herein in its entirety. DDD-028 was prepared as a suspension (1.0 mg/mL) in 5% PEG/5% Tween-80/90% saline; and pregabalin (reference compound, positive control) was prepared as a solution in normal saline (7.9 mg/mL). Both compounds were administered to the animals via oral gavage to a final dose of 5.0 mg/kg (17.4 gmol/kg) for DDD-028; and 39.0 mg/kg (250.2 gmol/kg) for pregabalin. Control animals received the vehicle (5% PEG/5% Tween-80/90% saline). Mechanical allodynia was measured by the up and down method using calibrated von Frey filaments (Linton Instruments). Eighteen male CD rats were used in this study. The animals were divided into three groups (vehicle, DDD-028, and pregabalin) containing 6 animals in each group. Baseline PWT measurements (pre-surgery) of the left-hind paw of each animal in the group were taken prior to spinal nerve ligation. Thereafter, the rats were anesthetized using 1-3% isofluorane, and the L5 spinal nerve was isolated and ligated tightly using silk thread. Peak mechano-allodynia generally develops by day 7 following surgery. After 7 days post-surgery, PWT measurements were taken for each animal to determine the extent of mechanical allodynia. Animals were then weighed, allocated to the treatment group, and administered the test compound, DDD-028, the reference compound, pregabalin, or the vehicle. PWT's were measured at 15 min, 30 min, 60 min, 120 min, and 180 min following administration of the drugs or vehicle. Results: DDD-028 significantly attenuated mechanical allodynia at 15 min, 30 min, 60 min, and 120 min post-adminstration with maximal anti-nociceptive effect occurring at about 60 minutes; the anti-nociceptive effect vanished at 180 min post administration (FIG. 5). DDD-028 appears to be about 5-fold more potent than pregabalin. No adverse effects were evident in the animals treated with the vehicle or DDD-028. Animals treated with pregabalin exhibited mild sedation 1-3 hours post-administration.

EXAMPLE 7

In Vivo Evaluation of Compound 13 (DDD-028) in CFA-Induced Inflammatory Pain Model Via Oral Administration of the Drug DDD-028 was evaluated in Complete Freund's Adjuvant (CFA)-induced model of inflammatory pain in rats as described by Stein et al. [24], which is incorporated herein in its entirety. Fifteen male CD rats were used in this study. The animals were divided into three groups (vehicle, DDD-028, and indomethacin) containing 5 animals in each group. Baseline weight distribution of each animal in the groups was measured taken prior to CFA administration. Three readings were taken for each paw in each animal. Each reading was take over 3 seconds. Animals were lifted or the paws adjusted between each reading to ensure that animals were positioned correctly on the force pads. The percent weight bearing was calculated on the left leg for each reading. The mean of the three readings were then calculated for each animal. Following baseline measurements, the rats were anesthetized using 1-3% isofluorane, and were given subplantar injection of 0.1 mL of CFA into the left hind paw. Percent weight distributions of the left hind paws of each animal in the three groups were measured at 24 hours post-administration to determine the extent of mechanical allodynia. Animals were then weighed, allocated to the treatment group, and administered the test compound, DDD-028, the reference compound, indomethacin, or the vehicle. Weight distributions were measured at 15 min, 30 min, 60 min, and 120 min following administration of the drugs or vehicle. Results: DDD-028 significantly attenuated mechanical allodynia at all time points post-administration with maximal anti-nociceptive effect occurring at about 60 minutes; the anti-nociceptive continue to persist even after 2 hours (FIG. 6). DDD-028 appears to be about 5-fold more potent than indomethacin. No adverse effects were evident in the animals treated with the vehicle or DDD-028. Animals treated with indomethacin exhibited mild sedation 2 hours post-administration.

REFERENCES

1. Fox, R. B.; Powell, W. H. *Nomenclature of Organic Compounds: Principles and Practice*, Second Edition. Oxford University Press, Oxford, 2001.
2. Hellwinkel, D. *Systematic Nomenclature of Organic Chemistry: A Directory of Comprehension and Application of its Basic Principles*. Springer-Verlag, Berlin, 2001.
3. American Psychiatric Association: *Diagnostic and Statistical Manual of Mental Disorders*, 4th Edition. Washington, D.C., Association, A. P., 1994.
4. Roth, B. L. Ed. *The Serotonin Receptors*. Humana Press, Totowa, N. J., 2006.
5. Nichols, D. E.; Nichols, C. D. *Chem. Rev.* 2008, 108, 1614.
6. Micale, V. et al. *Brain Res.* 2006, 112, 207.
7. Jongen-Relo, A. L. et al. *J. Soc. Neurosci. Annual Meet, Atlanta, Ga.* 2006, 526, 29.
8. King, M. V. et al. *Trends Pharmacol. Sci.* 2008, 29, 482.
9. Brenchat, A. et al. *Pain* 2010, 149, 483-494.
10. Mnie-Filali, O. et al. *Drug News Perspect.* 2007, 20, 613
11. Entrena, J. M et al. *Pain* 2009, 143, 252-261.
12. Crawford, K. W.; Bowen, W. D. *Cancer Research* 2002, 62, 313-322.
13. Rajagopalan, P. U.S. Pat. No. 4,438,120; 1984.
14. Rajagopalan, P. U.S. Pat. No. 4,219,550; 1980.
15. Adams, C. W. U.S. Pat. No. 3,983,123; 1976.
16. Bandyopadhyaya, A. et al. *Medicinal Chemistry Communications* 2012, 3, 580-583.
17. Bakuni, B. S. et al. *Organic Letters* 2012, 14, 2838-2841.
18. Pharmaceutical Manufacturing. In *Remington: The Science and Practice of Pharmacy*. Lippincott Williams & Wilkins, Philadelphia, 2005, 691-1058.

19. Weissig, V. *Liposomes: Methods and Protocols Volume 1: Pharmaceutical Nanocarriers.* Humana Press, New York, 2009.
20. Li, X. *Design of Controlled Release Drug Delivery Systems.* McGraw-Hill, New York, 2006.
21. Rautio, J. et al. *Nature Reviews Drug Discovery* 2008, 7, 255-270.
22. Bennett, G. J.; Xie, Y. K. *Pain* 1988, 33, 87-107.
23. Kim, S. H.; Chung, J. M. *Pain* 1992, 50, 355-363.
24. Stein, C.; Millan, M. J.; Herz, A. *Pharmacol. Biochem. Behav.* 1998, 31, 445-451.

I claim:
1. A compound of Formula I,

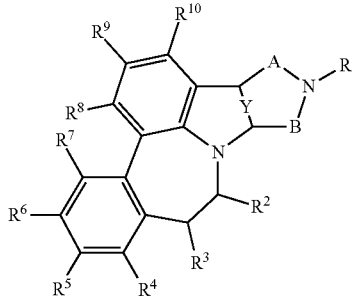

Formula I

Y is a single bond or a double bond;
A and B are independently —$(CH_2)_n$—;
subscript 'n' varies from 0 to 3;
$R^1$ is selected from the group consisting of hydrogen, $C_1$-$C_{10}$ alkyl, $C_1$-$C_{10}$ hydroxyalkyl, $C_5$-$C_{10}$ aryl, $C_1$-$C_{15}$ aroylalkyl, $C_1$-$C_{10}$ alkoxycarbonylalkyl, $C_5$-$C_{10}$ arylalkyl, and $C_1$-$C_{10}$ carbamoylalkyl;
$R^2$ is selected from the group consisting of hydrogen, $C_1$-$C_{10}$ alkyl, $C_5$-$C_{10}$ aryl, and $C_5$-$C_{10}$ arylalkyl;
each of $R^3$, $R^4$, $R^5$, $R^6$, $R^7$, $R^8$, $R^9$, and $R^{10}$ is independently selected from the group consisting of hydrogen, $C_1$-$C_{10}$ alkyl, hydroxyl, $C_1$-$C_{10}$ alkoxyl, —$NR^{11}R^{12}$, $C_1$-$C_{10}$ hydroxyalkyl, halogen, trihaloalkyl, cyano, carboxyl, $C_1$-$C_{10}$ acyl, $C_1$-$C_{10}$ alkoxyalkyl; $C_1$-$C_{10}$ alkoxycarbonyl, $C_5$-$C_{10}$ aryl, and $C_5$-$C_{10}$ arylalkyl; and
$R^{11}$ and $R^{12}$ are independently hydrogen or $C_1$-$C_{10}$ alkyl.
2. The compound of claim 1, wherein Y is a double bond;
A is —$CH_2$—; and
B is —$CH_2CH_2$—.
3. The compound of claim 2, wherein
$R^1$ is selected from the group consisting of hydrogen, $C_1$-$C_{10}$ alkyl, $C_1$-$C_{10}$ hydroxyalkyl, $C_5$-$C_{10}$ arylalkyl, and $C_1$-$C_{10}$ carbamoylalkyl;
$R^2$ and $R^3$ are hydrogens; and
each of $R^4$, $R^5$, $R^6$, $R^7$, $R^8$, $R^9$, and $R^{10}$ is independently selected from the group consisting of hydrogen, $C_1$-$C_{10}$ alkyl, hydroxyl, $C_1$-$C_{10}$ alkoxyl, and halogen.
4. The compound of claim 3, wherein
each of $R^4$, $R^5$, $R^6$, and $R^7$ is independently selected from the group consisting of hydrogen, $C_1$-$C_{10}$ alkyl, hydroxyl, $C_1$-$C_{10}$ alkoxyl, and halogen; and
$R^8$, $R^9$, and $R^{10}$ are hydrogens.
5. The compound of claim 3, wherein
$R^4$, $R^5$, $R^6$, and $R^7$ are hydrogens; and
each of $R^8$, $R^9$, and $R^{10}$ is independently selected from the group consisting of hydrogen, $C_1$-$C_{10}$ alkyl, hydroxyl, $C_1$-$C_{10}$ alkoxyl, and halogen.
6. The compound of claim 4, wherein
$R^1$ is hydrogen, $C_1$-$C_{10}$ alkyl, $CH_2Ph$, $CH_2CH_2OH$, or $CH_2CONH_2$; and
each of $R^4$, $R^5$, $R^6$, and $R^7$ is hydrogen, $CH_3$, hydroxyl, $OCH_3$, F, or Cl.
7. The compound of claim 5, wherein
$R^1$ is hydrogen, $C_1$-$C_{10}$ alkyl, $CH_2Ph$, $CH_2CH_2OH$, or $CH_2CONH_2$; and
each of $R^8$, $R^9$, and $R^{10}$ is hydrogen, $CH_3$, hydroxyl, $OCH_3$, F, or Cl.
8. The compound of claim 7, wherein $R^1$ is hydrogen or $CH_3$; and
$R^8$, $R^9$, and $R^{10}$ are hydrogens.
9. The compound of claim 1, wherein A is —$CH_2$—; B is —$CH_2CH_2$—;
and Y is a single bond with cis-fused B|C rings represented by the stereoisomeric structural Formulas IIa or IIb,

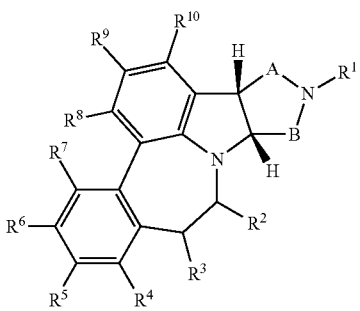

Formula IIa

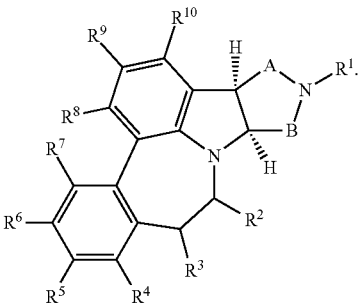

Formula IIb

10. The compound of claim 9, wherein
$R^1$ is selected from the group consisting of hydrogen, $C_1$-$C_{10}$ alkyl, $C_1$-$C_{10}$ hydroxyalkyl, $C_5$-$C_{10}$ arylalkyl, and $C_1$-$C_{10}$ carbamoylalkyl;
$R^2$ and $R^3$ are hydrogens; and
each of $R^4$, $R^5$, $R^6$, $R^7$, $R^8$, $R^9$, and $R^{10}$ is independently selected from the group consisting of hydrogen, $C_1$-$C_{10}$ alkyl, hydroxyl, $C_1$-$C_{10}$ alkoxyl, and halogen.
11. The compound of claim 10, wherein
each of $R^4$, $R^5$, $R^6$, and $R^7$ is independently selected from the group consisting of hydrogen, $C_1$-$C_{10}$ alkyl, hydroxyl, $C_1$-$C_{10}$ alkoxyl, and halogen; and
$R^8$, $R^9$, and $R^{10}$ are hydrogens.
12. The compound of claim 10, wherein
$R^4$, $R^5$, $R^6$, and $R^7$ are hydrogens; and
each of $R^8$, $R^9$, and $R^{10}$ is independently selected from the group consisting of hydrogen, $C_1$-$C_{10}$ alkyl, hydroxyl, $C_1$-$C_{10}$ alkoxyl, and halogen.
13. The compound of claim 11, wherein
$R^1$ is hydrogen, $C_1$-$C_{10}$ alkyl, $CH_2Ph$, $CH_2CH_2OH$, or $CH_2CONH_2$; and each of $R^4$, $R^5$, $R^6$, and $R^7$ is hydrogen, $CH_3$, hydroxyl, $OCH_3$, F, or Cl.

14. The compound of claim 12, wherein
$R^1$ is hydrogen, $C_1$-$C_{10}$ alkyl, $CH_2Ph$, $CH_2CH_2OH$, or $CH_2CONH_2$; and
each of $R^8$, $R^9$, and $R^{10}$ is hydrogen, $CH_3$, hydroxyl, $OCH_3$, F, or Cl.

15. The compound of claim 14, wherein $R^1$ is hydrogen or $CH_3$; and
$R^8$, $R^9$, and $R^{10}$ are hydrogens.

16. The compound of claim 1, wherein A is —$CH_2$—; B is —$CH_2CH_2$—;
and Y is a single bond with trans-fused B|C rings represented by the stereoisomeric structural Formulas IIIa or IIIb,

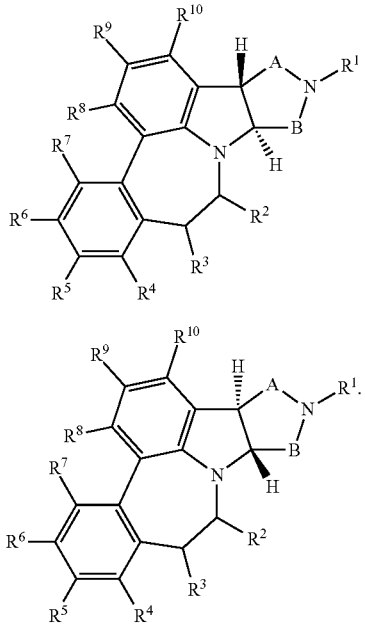

17. The compound of claim 16, wherein
$R^1$ is selected from the group consisting of hydrogen, $C_1$-$C_{10}$ alkyl, $C_1$-$C_{10}$ hydroxyalkyl, $C_5$-$C_{10}$ arylalkyl, and $C_1$-$C_{10}$ carbamoylalkyl;
$R^2$ and $R^3$ are hydrogens; and
each of $R^4$, $R^5$, $R^6$, $R^7$, $R^8$, $R^9$, and $R^{10}$ is independently selected from the group consisting of hydrogen, $C_1$-$C_{10}$ alkyl, hydroxyl, $C_1$-$C_{10}$ alkoxyl, and halogen.

18. The compound of claim 17, wherein
each of $R^4$, $R^5$, $R^6$, and $R^7$ is independently selected from the group consisting of hydrogen, $C_1$-$C_{10}$ alkyl, hydroxyl, $C_1$-$C_{10}$ alkoxyl, and halogen; and
$R^8$, $R^9$, and $R^{10}$ are hydrogens.

19. The compound of claim 17, wherein
$R^4$, $R^5$, $R^6$, and $R^7$ are hydrogens; and
each of $R^8$, $R^9$, and $R^{10}$ is independently selected from the group consisting of hydrogen, $C_1$-$C_{10}$ alkyl, hydroxyl, $C_1$-$C_{10}$ alkoxyl, and halogen.

20. The compound of claim 18, wherein
$R^1$ is hydrogen, $C_1$-$C_{10}$ alkyl, $CH_2Ph$, $CH_2CH_2OH$, or $CH_2CONH_2$; and
each of $R^4$, $R^5$, $R^6$, and $R^7$ is hydrogen, $CH_3$, hydroxyl, $OCH_3$, F, or Cl.

21. The compound of claim 19, wherein
$R^1$ is hydrogen, $C_1$-$C_{10}$ alkyl, $CH_2Ph$, $CH_2CH_2OH$, or $CH_2CONH_2$; and
each of $R^8$, $R^9$, and $R^{10}$ is hydrogen, $CH_3$, hydroxyl, $OCH_3$, F, or Cl.

22. The compound of claim 21, wherein $R^1$ is hydrogen or $CH_3$; and
$R^8$, $R^9$, and $R^{10}$ are hydrogens.

23. A pharmaceutical preparation comprising the compound of claim 8 in a pharmaceutically acceptable formulation for administration to a patient.

24. The pharmaceutical preparation of claim 8, in which the formulation is pharmaceutically acceptable for oral administration.

25. The pharmaceutical preparation of claim 8, in which the formulation is pharmaceutically acceptable for topical administration.

26. A method of alleviating pain comprising administering an effective amount of pharmaceutically acceptable composition of Formula I, wherein

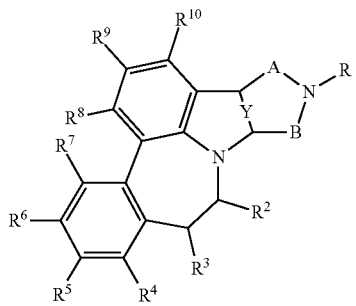

Y is a single bond or a double bond;
A and B are independently —$(CH_2)_n$—;
subscript 'n' varies from 0 to 3;
$R^1$ is selected from the group consisting of hydrogen, $C_1$-$C_{10}$ alkyl, $C_1$-$C_{10}$ hydroxyalkyl, $C_5$-$C_{10}$ aryl, $C_1$-$C_{15}$ aroylalkyl, $C_1$-$C_{10}$ alkoxycarbonylalkyl, $C_5$-$C_{10}$ arylalkyl, and $C_1$-$C_{10}$ carbamoylalkyl;
$R^2$ is selected from the group consisting of hydrogen, $C_1$-$C_{10}$ alkyl, $C_5$-$C_{10}$ aryl, and $C_5$-$C_{10}$ arylalkyl;
each of $R^3$, $R^4$, $R^5$, $R^6$, $R^7$, $R^8$, $R^9$, and $R^{10}$ is independently selected from the group consisting of hydrogen, $C_1$-$C_{10}$ alkyl, hydroxyl, $C_1$-$C_{10}$ alkoxyl, —$NR^{11}R^{12}$, $C_1$-$C_{10}$ hydroxyalkyl, halogen, trihaloalkyl, cyano, carboxyl, $C_1$-$C_{10}$ acyl, $C_1$-$C_{10}$ alkoxyalkyl; $C_1$-$C_{10}$ alkoxycarbonyl, $C_5$-$C_{10}$ aryl, and $C_5$-$C_{10}$ arylalkyl; and
$R^{11}$ and $R^{12}$ are independently hydrogen or $C_1$-$C_{10}$ alkyl.

27. The method of claim 26, wherein Y is a double bond;
A is —$CH_2$—; and
B is —$CH_2CH_2$—.

28. The method of claim 27, wherein
$R^1$ is selected from the group consisting of hydrogen, $C_1$-$C_{10}$ alkyl, $C_1$-$C_{10}$ hydroxyalkyl, $C_5$-$C_{10}$ arylalkyl, and $C_1$-$C_{10}$ carbamoylalkyl;
$R^2$ and $R^3$ are hydrogens; and
each of $R^4$, $R^5$, $R^6$, $R^7$, $R^8$, $R^9$, and $R^{10}$ is independently selected from the group consisting of hydrogen, $C_1$-$C_{10}$ alkyl, hydroxyl, $C_1$-$C_{10}$ alkoxyl, and halogen.

29. The method of claim 28, wherein
each of $R^4$, $R^5$, $R^6$, and $R^7$ is independently selected from the group consisting of hydrogen, $C_1$-$C_{10}$ alkyl, hydroxyl, $C_1$-$C_{10}$ alkoxyl, and halogen; and
$R^8$, $R^9$, and $R^{10}$ are hydrogens.

30. The method of claim 28, wherein
R$^4$, R$^5$, R$^6$, and R$^7$ are hydrogens; and
each of R$^8$, R$^9$, and R$^{10}$ is independently selected from the group consisting of hydrogen, C$_1$-C$_{10}$ alkyl, hydroxyl, C$_1$-C$_{10}$ alkoxyl, and halogen.

31. The method of claim 29, wherein
R$^1$ is hydrogen, C$_1$-C$_{10}$ alkyl, CH$_2$Ph, CH$_2$CH$_2$OH, or CH$_2$CONH$_2$; and
each of R$^4$, R$^5$, R$^6$, and R$^7$ is hydrogen, CH$_3$, hydroxyl, OCH$_3$, F, or Cl.

32. The method of claim 30, wherein
R$^1$ is hydrogen, C$_1$-C$_{10}$ alkyl, CH$_2$Ph, CH$_2$CH$_2$OH, or CH$_2$CONH$_2$; and
each of R$^8$, R$^9$, and R$^{10}$ is hydrogen, CH$_3$, hydroxyl, OCH$_3$, F, or Cl.

33. The method of claim 32, wherein R$^1$ is hydrogen or CH$_3$; and
R$^8$, R$^9$, and R$^{10}$ are hydrogens.

34. The method of claim 26, wherein A is —CH$_2$—; B is —CH$_2$CH$_2$—;
and Y is a single bond with cis-fused B|C rings represented by the stereoisomeric structural Formulas IIa or IIIb,

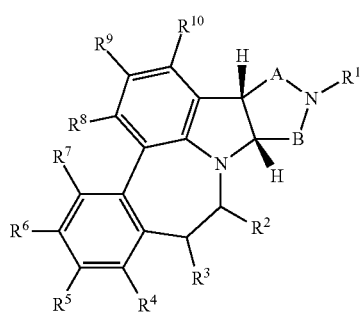

Formula IIa

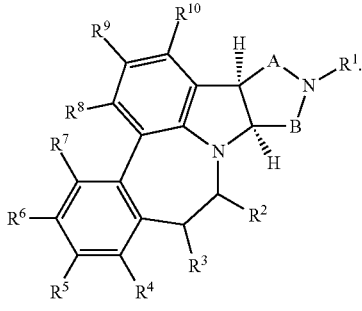

Formula IIb

35. The method of claim 34, wherein
R$^1$ is selected from the group consisting of hydrogen, C$_1$-C$_{10}$ alkyl, C$_1$-C$_{10}$ hydroxyalkyl, C$_5$-C$_{10}$ arylalkyl, and C$_1$-C$_{10}$ carbamoylalkyl;
R$^2$ and R$^3$ are hydrogens; and
each of R$^4$, R$^5$, R$^6$, R$^7$, R$^8$, R$^9$, and R$^{10}$ is independently selected from the group consisting of hydrogen, C$_1$-C$_{10}$ alkyl, hydroxyl, C$_1$-C$_{10}$ alkoxyl, and halogen.

36. The method of claim 35, wherein
each of R$^4$, R$^5$, R$^6$, and R$^7$ is independently selected from the group consisting of hydrogen, C$_1$-C$_{10}$ alkyl, hydroxyl, C$_1$-C$_{10}$ alkoxyl, and halogen; and
R$^8$, R$^9$, and R$^{10}$ are hydrogens.

37. The method of claim 35, wherein
R$^4$, R$^5$, R$^6$, and R$^7$ are hydrogens; and
each of R$^8$, R$^9$, and R$^{10}$ is independently selected from the group consisting of hydrogen, C$_1$-C$_{10}$ alkyl, hydroxyl, C$_1$-C$_{10}$ alkoxyl, and halogen.

38. The method of claim 36, wherein
R$^1$ is hydrogen, C$_1$-C$_{10}$ alkyl, CH$_2$Ph, CH$_2$CH$_2$OH, or CH$_2$CONH$_2$; and
each of R$^4$, R$^5$, R$^6$, and R$^7$ is hydrogen, CH$_3$, hydroxyl, OCH$_3$, F, or Cl.

39. The method of claim 37, wherein
R$^1$ is hydrogen, C$_1$-C$_{10}$ alkyl, CH$_2$Ph, CH$_2$CH$_2$OH, or CH$_2$CONH$_2$; and
each of R$^8$, R$^9$, and R$_{10}$ is hydrogen, CH$_3$, hydroxyl, OCH$_3$, F, or Cl.

40. The method of claim 39, wherein R$^1$ is hydrogen or CH$_3$; and
R$^8$, R$^9$, and R$^{10}$ are hydrogens.

41. The method of claim 26, wherein A is —CH$_2$—; B is —CH$_2$CH$_2$—;
and Y is a single bond with trans-fused B|C rings represented by the stereoisomeric structural Formulas IIIa or IIIb,

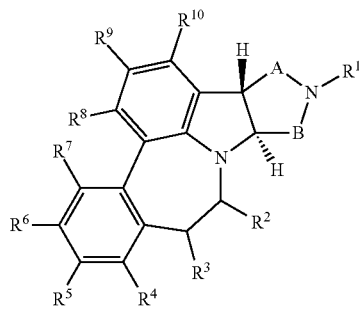

Formula IIIa

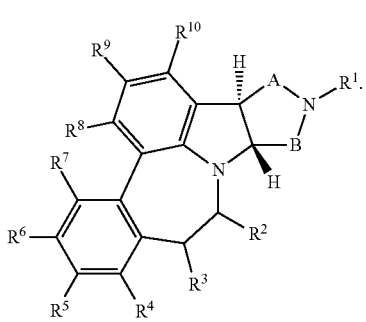

Formula IIIb

42. The method of claim 41, wherein
R$^1$ is selected from the group consisting of hydrogen, C$_1$-C$_{10}$ alkyl, C$_1$-C$_{10}$ hydroxyalkyl, C$_5$-C$_{10}$ arylalkyl, and C$_1$-C$_{10}$ carbamoylalkyl;
R$^2$ and R$^3$ are hydrogens; and
each of R$^4$, R$^5$, R$^6$, R$^7$, R$^8$, R$^9$, and R$^{10}$ is independently selected from the group consisting of hydrogen, C$_1$-C$_{10}$ alkyl, hydroxyl, C$_1$-C$_{10}$ alkoxyl, and halogen.

43. The method of claim 42, wherein
each of R$^4$, R$^5$, R$^6$, and R$^7$ is independently selected from the group consisting of hydrogen, C$_1$-C$_{10}$ alkyl, hydroxyl, C$_1$-C$_{10}$ alkoxyl, and halogen; and
R$^8$, R$^9$, and R$^{10}$ are hydrogens.

44. The method of claim 42, wherein
R$^4$, R$^5$, R$^6$, and R$^7$ are hydrogens; and
each of R$^8$, R$^9$, and R$^{10}$ is independently selected from the group consisting of hydrogen, C$_1$-C$_{10}$ alkyl, hydroxyl, C$_1$-C$_{10}$ alkoxyl, and halogen.

45. The method of claim 43, wherein
R$^1$ is hydrogen, C$_1$-C$_{10}$ alkyl, CH$_2$Ph, CH$_2$CH$_2$OH, or CH$_2$CONH$_2$; and
each of R$^4$, R$^5$, R$^6$, and R$^7$ is hydrogen, CH$_3$, hydroxyl, OCH$_3$, F, or Cl.

46. The method of claim 44, wherein
$R^1$ is hydrogen, $C_1$-$C_{10}$ alkyl, $CH_2Ph$, $CH_2CH_2OH$, or $CH_2CONH_2$; and
each of $R^8$, $R^9$, and $R^{10}$ is hydrogen, $CH_3$, hydroxyl, $OCH_3$, F, or Cl.

47. The method of claim 46, wherein $R^1$ is hydrogen or $CH_3$; and
$R^8$, $R^9$, and $R^{10}$ are hydrogens.

48. The method of claim 26, wherein said pain arises from neuropathy.

49. The method of claim 26, wherein said pain arises from inflammation.

50. The method of claim 26, wherein said pain arises from arthritis.

51. The method of claim 26, wherein said pain arises from cancer.

* * * * *